(12) United States Patent
Xiang

(10) Patent No.: US 7,238,588 B2
(45) Date of Patent: Jul. 3, 2007

(54) SILICON BUFFERED SHALLOW TRENCH ISOLATION

(75) Inventor: Qi Xiang, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 178 days.

(21) Appl. No.: 10/755,746

(22) Filed: Jan. 12, 2004

(65) Prior Publication Data

US 2005/0095807 A1    May 5, 2005

Related U.S. Application Data

(63) Continuation-in-part of application No. 10/389,456, filed on Mar. 14, 2003, and a continuation-in-part of application No. 10/358,966, filed on Feb. 5, 2003, now Pat. No. 6,962,857, and a continuation-in-part of application No. 10/341,848, filed on Jan. 14, 2003, now Pat. No. 6,673,696, and a continuation-in-part of application No. 10/341,863, filed on Jan. 14, 2003.

(51) Int. Cl.
*H01L 21/762* (2006.01)
(52) U.S. Cl. .............................. 438/431; 257/E21.547
(58) Field of Classification Search ................ 438/424, 438/425, 430, 431; 257/E21.547
See application file for complete search history.

(56) References Cited

U.S. PATENT DOCUMENTS

| | | | |
|---|---|---|---|
| 5,254,873 A | 10/1993 | Poon et al. |
| 5,266,813 A | 11/1993 | Comfort et al. |
| 5,406,111 A | 4/1995 | Sun |
| 5,455,194 A | 10/1995 | Vasquez et al. |
| 5,668,044 A | 9/1997 | Ohno |
| 5,700,712 A | 12/1997 | Schwalke |
| 5,719,085 A | 2/1998 | Moon et al. |
| 5,793,090 A | 8/1998 | Gardner et al. |
| 5,837,612 A | 11/1998 | Ajuria et al. |
| 6,013,937 A | 1/2000 | Beintner et al. |
| 6,037,238 A | 3/2000 | Chang et al. |
| 6,074,930 A | 6/2000 | Cho et al. |
| 6,074,931 A | 6/2000 | Chang et al. |

(Continued)

FOREIGN PATENT DOCUMENTS

EP        0 245 622 B1     11/1987

(Continued)

OTHER PUBLICATIONS

Vossen John L. and Kern Werner, "Thin Film Processing II" Academic Press 1991 pp. 134 and 371.*

(Continued)

*Primary Examiner*—Stephen W. Smoot
(74) *Attorney, Agent, or Firm*—Foley & Lardner LLP

(57) ABSTRACT

A method of manufacturing an integrated circuit (IC) utilizes a shallow trench isolation (STI) technique. The shallow trench isolation technique is used in strained silicon (SMOS) process. The liner for the trench is formed from a semiconductor or metal layer which is formed in a selective epitaxial growth (SEG) process. The SEG process can be a CVD or MBE process. Capping layers can be used above the strained silicon layer.

19 Claims, 4 Drawing Sheets

U.S. PATENT DOCUMENTS

| | | | |
|---|---|---|---|
| 6,080,618 | A | 6/2000 | Bergner et al. |
| 6,080,627 | A | 6/2000 | Fan et al. |
| 6,080,637 | A | 6/2000 | Huang et al. |
| 6,087,705 | A | 7/2000 | Gardner et al. |
| 6,107,143 | A | 8/2000 | Park et al. |
| 6,136,664 | A | 10/2000 | Economikos et al. |
| 6,146,970 | A | 11/2000 | Witek et al. |
| 6,150,212 | A | 11/2000 | Divakaruni et al. |
| 6,168,961 | B1 | 1/2001 | Vaccari |
| 6,207,531 | B1 | 3/2001 | Pen-Liang |
| 6,214,696 | B1 | 4/2001 | Wu |
| 6,271,143 | B1 | 8/2001 | Mendicino |
| 6,306,722 | B1 | 10/2001 | Yang et al. |
| 6,391,731 | B1 | 5/2002 | Chong et al. |
| 6,399,512 | B1 | 6/2002 | Blosse et al. |
| 6,414,364 | B2 | 7/2002 | Lane et al. |
| 6,426,278 | B1 | 7/2002 | Nowak et al. |
| 6,456,370 | B1 | 9/2002 | Ingles, Jr. |
| 6,468,853 | B1 | 10/2002 | Balasubramanian et al. |
| 6,498,383 | B2 | 12/2002 | Beyer et al. |
| 6,524,931 | B1 | 2/2003 | Perera |
| 6,548,261 | B1 | 4/2003 | Smith et al. |
| 6,548,361 | B1 | 4/2003 | En et al. |
| 6,566,228 | B1 | 5/2003 | Beintner et al. |
| 6,613,646 | B1 | 9/2003 | Sahota et al. |
| 6,646,322 | B2 | 11/2003 | Fitzgerald |
| 6,656,749 | B1 | 12/2003 | Paton et al. |
| 6,664,574 | B2 * | 12/2003 | Azam et al. ............... 257/197 |
| 6,673,696 | B1 | 1/2004 | Arasnia et al. |
| 6,706,581 | B1 | 3/2004 | Bou et al. |
| 7,029,988 | B2 * | 4/2006 | Ohnishi et al. ............ 438/424 |
| 2002/0045312 | A1 | 4/2002 | Zheng et al. |
| 2002/0098689 | A1 | 7/2002 | Chong et al. |
| 2003/0049893 | A1 | 3/2003 | Currie et al. |
| 2003/0139051 | A1 | 7/2003 | Andideh et al. |
| 2004/0061161 | A1 | 4/2004 | Radens et al. |
| 2004/0089914 | A1 | 5/2004 | Mouli et al. |

FOREIGN PATENT DOCUMENTS

| | | |
|---|---|---|
| GB | 2 254 731 A | 10/1992 |
| WO | WO 02/095818 A1 | 11/2002 |
| WO | WO 02/101818 A2 | 12/2002 |

OTHER PUBLICATIONS

John L. Vossen Thin Flim Processes II Academic Press 1991 p. 336.*

Stanley Wolf and Richard N. Tauber, "Silicon Processing for the VLSI Era—vol. 1: Process Technology," pp. 124-125, 182-183, Lattice Press, Sunset Beach, California (1986).*

International Search Report for PCT/US2004/000982, 4 pages.

Written Opinion of the International Searching Authority; International Application No. PCT/US2004/007464; International Filing Date Mar. 11, 2004; 6 pgs.

International Search Report; International Application No. PCT/US2004/007464; mailed Jan. 9, 2004; 3 pgs.

Ohkubo, Satoshi; Tamura Yasuyuki; Sugino, Rinji; Nakanishi, Toshiro; Sugita, Yoshihiro; Awaji, Naoki and Takasaki, Kanetake; "High Quality Ultra-Thin (4nm) Gate Oxide by UV/O$_3$ Surface Pre-Treatment of Native Oxide"; 1995 Symposium On VLSI Technology; Digest of Technical Papers; Jun. 6-8, 1995; Kyoto, Japan; 3 pgs.

Written Opinion of the International Searching Authority; International Application No. PCT/US2004/000982; International Filing Date Jan. 13, 2004; 6 pgs.

Wolf, Stanley, Ph.D. and Tauber, Richard N., Ph.D.; "Silicon Processing For The VLSI Era"; vol. 1: Process Technology; Lattice Press; 1986; pp. 57-58, 194.

Ghandhi, Sorab K. "VLSI Fabrication Principles"; John Wiley and Sons; 1983; pp. 422-423.

U.S. Appl. No. 10/389,456, filed Mar. 14, 2003, entitled "Shallow Trench Isolation For Strained Silicon Processes" (37 pgs.).

U.S. Appl. No. 10/341,848, filed Jan. 14, 2003, entitled "Post Trench Fill Oxidation Process for Strained Silicon Processes" (17 pgs.); Amendment to Specification (1 pg.).

U.S. Appl. No. 10/358,966, filed Feb. 5, 2003, entitled "Shallow Trench Isolation Process For Strained Silicon Processes" (23 pgs.).

U.S. Appl. No. 10/341,863, filed Jan. 14, 2003, entitled "Shallow Trench Isolation for Strained Silicon Processes" (26 pgs.); Amendment to Specification (1 pg.).

U.S. Appl. No. 10/620,194, filed Jul. 15, 2003, entitled "Front Side Seal to Prevent Germanium Outgassing"; (21 pgs.); Amendment to Specification (1 pg.).

Van Zant, Peter, "Microchip Fabrication", McGraw Hill, 1977, pp. 31 and 39.

Vossen, John L. and Kern, Werner, "Thin Film Processes II"; Academic Press, 1991, p. 333.

Rim, K., Welser, J., Hoyt, J.L., and Gibbons, J.F., "Enhanced Hole Mobilities in Surface-channel Strained-Si p-MOSFETs", 1995 International Electron Devices Meeting Technical Digest, 5 pages.

Wesler, J., Hoyt, J.L., Takagi, S. and Gibbons, J.F., "Strain Dependence of the Performance Enhancment in Strained-Si n-MOSFETs", 1994 International Electron Devices Meeting Technical Digest, San Francisco, CA Dec. 11-14, 1994, 5 pages.

* cited by examiner

US 7,238,588 B2

SILICON BUFFERED SHALLOW TRENCH ISOLATION

CROSS REFERENCE TO RELATED APPLICATIONS

The present application is a continuation-in-part of U.S. application Ser. No. 10/389,456, filed by Wang et al. on Mar. 14, 2003 and entitled "Shallow Trench Isolation for Strained Silicon Processes"; U.S. application Ser. No. 10/341,863, filed by Ngo et al. on Jan. 14, 2003 and entitled "Shallow Trench Isolation for Strained Silicon Processes"; U.S. application Ser. No. 10/358,966, filed on Feb. 5, 2003 now U.S. Pat. No. 6,962,857 by Lin et al. and entitled "Shallow Trench Isolation Process Using Oxide Deposition and Anneal for Strained Silicon Processes"; and U.S. application Ser. No. 10/341,848, filed on Jan. 14, 2003 now U.S. Pat. No. 6,673,696 by Arasnia et al. and entitled "Post Trench Fill Oxidation Process for Strained Silicon Processes"; all of which are assigned to the Assignee of the present application.

FIELD OF THE INVENTION

The present application is related to integrated circuit (IC) devices and to processes of making IC devices. More particularly, the present application relates to a method of forming trench isolation structures on substrates or layers including germanium.

BACKGROUND OF THE INVENTION

Integrated circuits (ICs) include a multitude of transistors formed on a semiconductor substrate. Various methods of forming transistors on a semiconductor substrate are known in the art. Generally, transistors are isolated from each other by insulating or isolation structures.

One method of forming insulating structures and defining source and drain regions is by utilizing a shallow trench isolation (STI) process. A conventional STI process typically includes the following simplified steps. First, a silicon nitride layer is thermally grown or deposited onto the silicon substrate. Next, using a lithography and etch process, the silicon nitride layer is selectively removed to produce a pattern where transistor source/drain areas are to be located. After patterning the source/drain areas, the substrate is etched to form trenches. After the trenches are formed, a liner oxide is thermally grown on the exposed surfaces of the trench. The liner oxide is typically formed at a very high temperature in a hydrochloric acid (HCl) ambient. An insulative material such as silicon dioxide ($SiO_2$) is blanket deposited over the nitride layer and the liner oxide within the trench. The insulative material is polished to create a planar surface. The nitride layer is subsequently removed to leave the oxide structures within the trenches.

Shallow trench isolation (STI) structures are utilized in strained silicon (SMOS) processes. SMOS processes are utilized to increase transistor (MOSFET) performance by increasing the carrier mobility of silicon, thereby reducing resistance and power consumption and increasing drive current, frequency response, and operating speed. Strained silicon is typically formed by growing a layer of silicon on a silicon germanium substrate or layer.

Theoretical calculations indicate that strained silicon layers in biaxial tension should exhibit higher electron and hole mobilities than do bulk silicon layers. It has been theoretically and experimentally demonstrated that mobilities are enhanced when the silicon layer is grown pseudomorphically on relaxed silicon germanium, which has a larger in-plane lattice constant than bulk silicon. Enhanced performance is demonstrated in SMOS transistors with channel regions formed by strained silicon on relaxed silicon germanium as discussed in "Strained Dependence of the Performance Enhancement in Strained-Si n-MOSFETS", J. Welser, et al., IEDM'94, p. 373, 1994 and "Enhanced Hole Mobilities in Surface-Channel Strained-Si p-MOSFETS", K. Rim, et al., IEDM'95, p. 517, 1995.

The silicon germanium lattice associated with the silicon germanium substrate is generally more widely spaced than a pure silicon lattice, with spacing becoming wider with a higher percentage of germanium. Because the silicon lattice aligns with the larger silicon germanium lattice, a tensile strain is created in the silicon layer. The silicon atoms are essentially pulled apart from one another.

Relaxed silicon has a conductive band that contains six equal valence bands. The application of tensile strain to the silicon causes four of the valence bands to increase in energy and two of the valence bands to decrease in energy. As a result of quantum effects, electrons effectively weigh 30 percent less when passing through the lower energy bands. Thus, the lower energy bands offer less resistance to electron flow. In addition, electrons meet with less vibrational energy from the nucleus of the silicon atom, which causes them to scatter at a rate of 500 to 1000 times less than in relaxed silicon. As a result, carrier mobility is dramatically increased in strained silicon compared to relaxed silicon, providing an increase in mobility of 80% or more for electrons and 20% or more for holes. The increase in mobility has been found to persist for current fields up to 1.5 megavolts/centimeter. These factors are believed to enable a device speed increase of 35% without further reduction of device size, or a 25% reduction in power consumption without a reduction in performance.

STI structures are the state-of-the-art isolation structures that have been widely applied to very large scale integrated (VLSI) and ultra large scale (ULSI) integrated circuits. One problem associated with STI structures involves the formation of sharp corners at the top of the trenches, which can result in transistor leakage currents and degraded gate oxide integrity. To avoid these problems, semiconductor fabrication techniques have been used to round the corners of such trenches to increase the radius of curvature and thereby decrease the electric field at the corners of the trenches.

Conventional processes have rounded the corners of the trenches by oxidizing the entire inner surface of the newly formed trench (e.g., by forming an oxide liner before filling the trench). Generally, the exposed corners of the silicon layer associated with the trenches oxidize faster than a flat surface in the silicon layer, thus forming a rounded upper corner at the top of the trench. This oxidation process is referred to as a liner oxidation process.

Using liner oxidation to achieve corner rounding in strained silicon devices can result in additional problems due to the presence of the silicon germanium layer under the active (strained) silicon layer. In silicon/silicon germanium devices, the shallow trench is etched through the silicon layer (approximately 200 Å) into the silicon germanium layer to achieve a total trench depth of between approximately 2,000–4,000 Å. When the exposed portion of the silicon germanium on the sidewalls of the newly formed trench is oxidized during the process of rounding the corners, the presence of germanium dramatically increases the oxidation rate relative to bulk silicon, thereby resulting in a non-uniform oxide thickness between the silicon layer and the silicon germanium layer.

Another problem related to liner oxidation in SMOS devices is germanium build-up. The build-up of germanium essentially forms a high concentration germanium layer along the side walls and bottom of the trenches between the liner oxide and the silicon germanium layer. The high concentration germanium layer can change the electrical characteristics of the STI structure. One change in electrical characteristics can be a higher junction leakage.

The use of germanium in SMOS processes can also cause germanium contamination problems for IC structures, layers, and equipment. In particular, germanium outgassing or outdiffusion can contaminate various components associated with the fabrication equipment and integrated circuit structures associating with the processed wafer. Further, germanium outgassing can negatively impact the formation of thin films.

Germanium outgassing can be particularly problematic at the very high temperatures and HCI ambient environments associated with the liner of a shallow trench isolation (STI) structure. For example, conventional STI liner oxide processes can utilize temperatures of approximately 1000° C., which act to enhance germanium outgassing.

Thus, there is a need for an STI structure with a liner that does not have a non-uniform thickness between the silicon and the silicon germanium layers. Further still, there is a need for a process of forming high quality oxides with good compatibility and that are not susceptible to germanium outgassing. Further still, there is a need for an efficient SMOS trench liner formation process. Yet further, there is a need for a liner formation process that is not as susceptible to a high concentration of germanium between the silicon dioxide liner and the silicon germanium layer. Further still, there is a need for an STI process that does not utilize high temperature to thermally grow liners.

SUMMARY OF THE INVENTION

An exemplary embodiment relates to a method of manufacturing an integrated circuit. The integrated circuit includes trench isolation regions in a substrate including germanium. The method includes forming a mask layer above the substrate, and selectively etching the mask layer to form apertures associated with locations of the trench isolation (STI) regions. The method also includes forming trenches in the substrate at the locations, providing a semiconductor or metal layer within the trenches by selective epitaxial growth, and forming oxide liners using the semiconductor or metal layer in the trenches of the substrate.

Yet another exemplary embodiment relates to a method of forming shallow trench isolation regions in a semiconductor layer. The method includes providing a hard mask layer above the semiconductor layer, providing a photoresist layer above the hard mask layer, and selectively removing portions of the photoresist layer in a photolithographic process. The method further includes removing the hard mask layer at the locations, forming trenches in the hard mask layer under the locations, providing a conformal semiconductor layer in the trenches, and oxidizing to form a liner in the trenches.

Yet another exemplary embodiment relates to a method of forming a liner in a trench in a germanium containing layer. The method includes selectively etching the germanium containing layer to form the trench, providing a semiconductor layer in the trench, and forming an oxide liner from the semiconductor layer.

BRIEF DESCRIPTION OF THE DRAWINGS

Exemplary embodiments will become more fully understood from the following detailed description, taken in conjunction with the accompanying drawings, wherein like reference numerals refer to like parts, and wherein.

DETAILED DESCRIPTION OF REFERRED EXEMPLARY EMBODIMENTS

Figure 1:
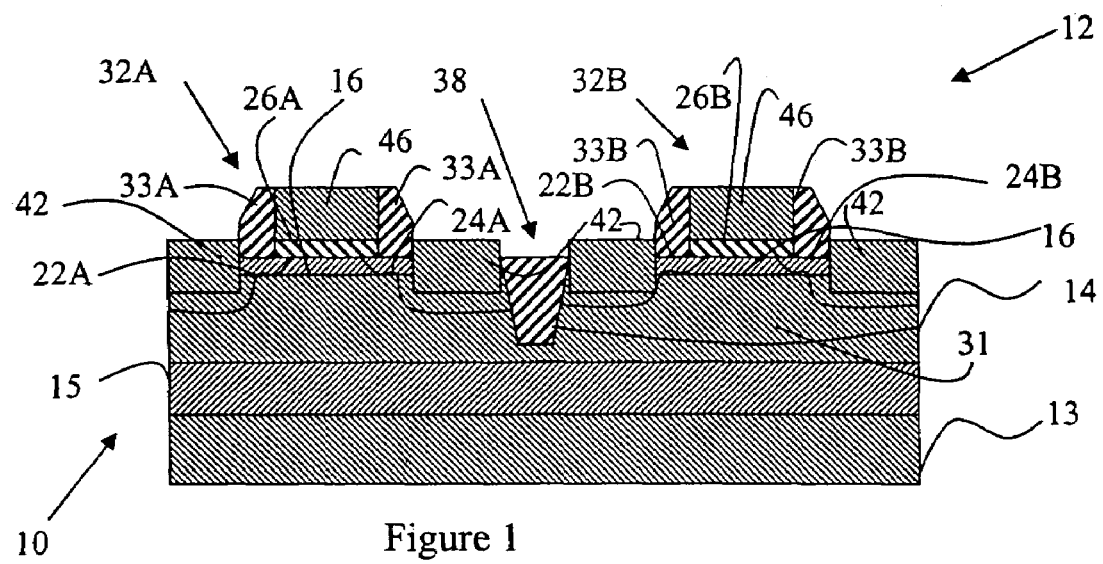
FIG. 1 is a cross-sectional view schematic drawing of a portion of an integrated circuit including an NMOS transistor and a PMOS transistor above a strained silicon layer and separated by a shallow trench/solution (STI) structure in accordance with an exemplary embodiment.

FIGS. 1 through 9 illustrate a method of manufacturing an integrated circuit (IC) in accordance with an exemplary embodiment. The method illustrated in FIGS. 1 through 9 reduces germanium outgassing and outdiffusion problems associated with silicon germanium layers or structures. The process can be used in a shallow trench isolation (STI) process or in any process requiring a liner oxide and utilizing germanium or other substances prone to outgassing at high temperatures. Advantageously, a liner oxide layer can be formed from a buffer layer and yet provide a high quality oxide with good compatibility. The buffer layer reduces germanium outgassing, reduces non-uniform liner thicknesses on silicon and silicon-germanium sidewalls, and prevents the formation of a high concentration germanium layer between the liner and the silicon-germanium sidewall.

Referring to FIGS. 1 through 9, a cross-sectional view of a portion 12 (FIG. 1) of an integrated circuit (IC) 10 is subjected to process 100 (FIG. 9) to form a shallow trench isolation (STI) structure 38. Portion 12 of integrated circuit 10 includes an NMOS transistor associated with a gate structure 32A and a PMOS transistor associated with a gate structure 32B.

Gate structures 32A and 32B are provided above a strained layer 16. Layer 16 can be a strained silicon layer. Strained silicon layer 16 is provided above a compound layer such as a silicon germanium substrate or layer 14. Layer 14 can be a relaxed silicon germanium layer.

Silicon germanium layer 14 is provided above a graded silicon germanium buffer layer 15. Layer 15 is provided above a silicon substrate 13. Layer 15 has a relatively low concentration of germanium at a bottom surface next to substrate 13 and a relatively high concentration of germanium (e.g., the same level as layer 14) at a top surface next to layer 16.

Gate structures 32A and 32B are provided between source regions 22A–B and drain regions 24A–B, respectively. A silicide layer 42 can be provided above source regions 22A–B and drain regions 24A–B. STI structure 38 separates the NMOS and PMOS transistors.

The transistor associated with gate structure 32B can be provided in an N well 31. N well 31 preferably extends into silicon germanium layer 14 and layer 14 is between approximately 0.5 micron and 5 micron Å deep. Source regions 22A–B and drain regions 24A–B preferably extend through layer 16 and into layer 14.

STI structure 38 preferably includes deposited silicon dioxide provided above an oxide liner manufactured according to process 100. STI structure 38 can be between approximately 1500–3000 Å deep and between approximately 150 nm and 300 nm Å wide. Gate structures 32A and 32B include spacers 33A–B, respectively, gate conductors 46, and gate dielectric layers 26A–B, respectively. Structure 38 is preferably deeper than well 31.

The various structures associated with the NMOS and PMOS transistors shown in FIG. 1 can be manufactured by a variety of processes. For example, conventional processes can be utilized to form layer 42, spacers 33A–B, gate conductors 46, etc., without departing from the scope of the invention. Further, STI structure 38 does not necessarily have to isolate NMOS and PMOS structures, and can be utilized to isolate different types of transistors or transistors of the same type.

Trench or STI structure 38 preferably includes rounded corners 64 (FIG. 7) associated with the interface of structure 38 with a top surface of layer 16. Layer 16 can be a 100–500 Å thick layer of strained silicon. Layer 15 can have a thickness between approximately 1000 Å and 1 micron.

Figure 2:
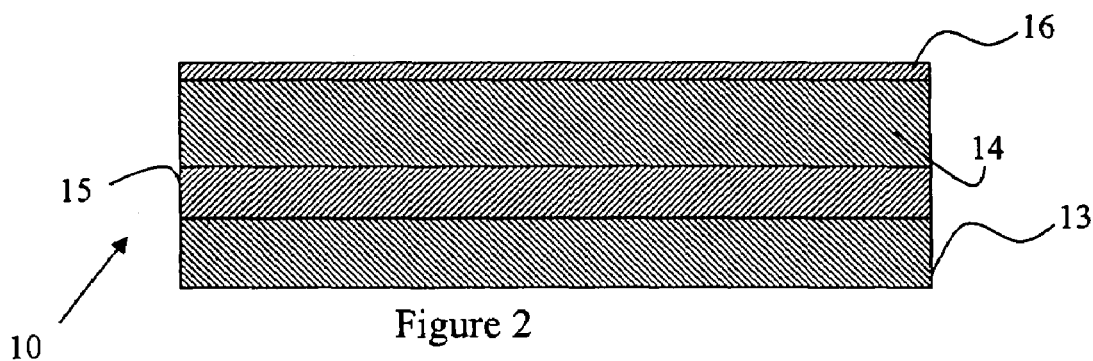
FIG. 2 is a cross-sectional schematic view of the portion illustrated in FIG. 1, showing the portion including a strained silicon layer, a silicon-germanium layer, a silicon-germanium graded layer, and a silicon substrate.

In FIG. 2, portion 12 includes a strained silicon layer 16. Layer 16 is provided over a semiconductor substrate or a germanium-containing layer 14. Layer 14 can be provided above silicon-germanium buffer layer 15. Layer 15 is provided above a substrate 13.

Substrate 13 is optional, and portion 12 can be provided with layer 14 or layer 15 as the bottom-most layer. Substrate 13 can be the same material or a different material than layer 14. In one embodiment, substrate 13 is a semiconductor substrate such as a silicon substrate upon which silicon germanium layer 14 has been grown above layer 15.

Layer 14 is preferably silicon germanium or another semiconductor material including germanium, and can be doped with P-type dopants or N-type dopants. Layer 14 can be an epitaxial layer provided on layer 15. Layer 15 can be an epitaxial layer provided above a semiconductor or an insulative base, such as substrate 13. Furthermore, layer 14 is preferably a composition of silicon germanium ($Si_{1-x}Ge_x$, where X is approximately 0.2 and is more generally in the range of 0.1–0.4). Layers 14 and 15 can be grown or deposited.

In one embodiment, layers 14 and 15 are grown above layer 13 by chemical vapor deposition (CVD) using disilane ($Si_2H_6$) and germane ($Ge_eH_4$) as source gases with a substrate temperature of approximately 650° C. Layer 14 can be grown at a disilane partial pressure of 30 mPa and a germane partial pressure of 60 mPa. Growth of silicon germanium material for layer 14 may be initiated using these ratios. For layer 15, the partial pressure of germanium may be gradually increased beginning from a lower pressure or zero pressure to form a gradient composition. Alternatively, a silicon layer can be doped by ion implantation with germanium or other processes can be utilized to form layer 14. Preferably, layer 14 is grown by epitaxy to a thickness of less than approximately 2 micron (and preferably between approximately 500 Å and 2 micron).

A strained silicon layer 16 is formed above layer 14 by an epitaxial process. Preferably, layer 16 is grown by CVD at a temperature of approximately 600° C. or less. Layer 16 can be a pure silicon layer and have a thickness of between approximately 50 and 150 Å.

In one embodiment, for pseudomorphic growth of strained-silicon layers such as layer 16 on relaxed silicon germanium layer (e.g., layer 14), a critical strained-silicon layer thickness exists. To grow defect-free strained-silicon on relaxed silicon germanium, the strained-silicon layer should be less than the critical thickness. This critical thickness is dependent upon germanium content and relaxed-silicon germanium layer. For SMOS applications, the germanium content is about 20–30% and the critical thickness is less than 200 Å. In one embodiment, the germanium content of layer 14 is 20–30% and the thickness of layer 16 is less than 200 Å.

Figure 3:
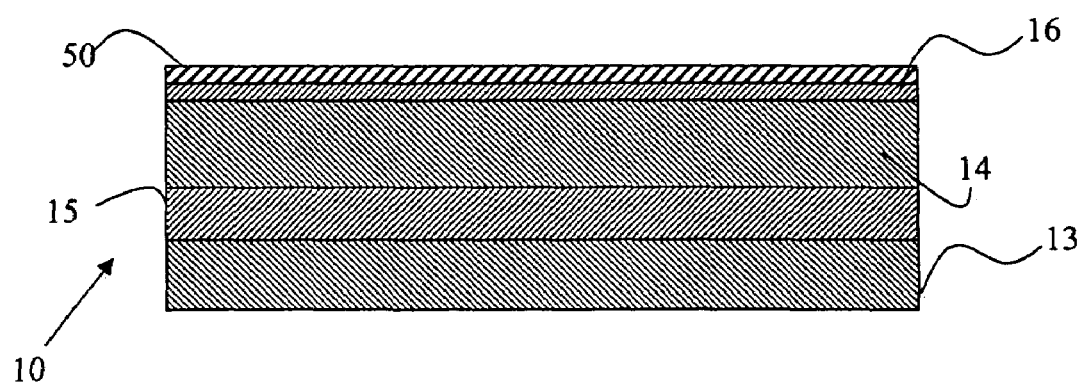
FIG. 3 is a cross-sectional schematic view of the portion illustrated in FIG. 2, showing a buffer oxide deposition step.
Figure 9:
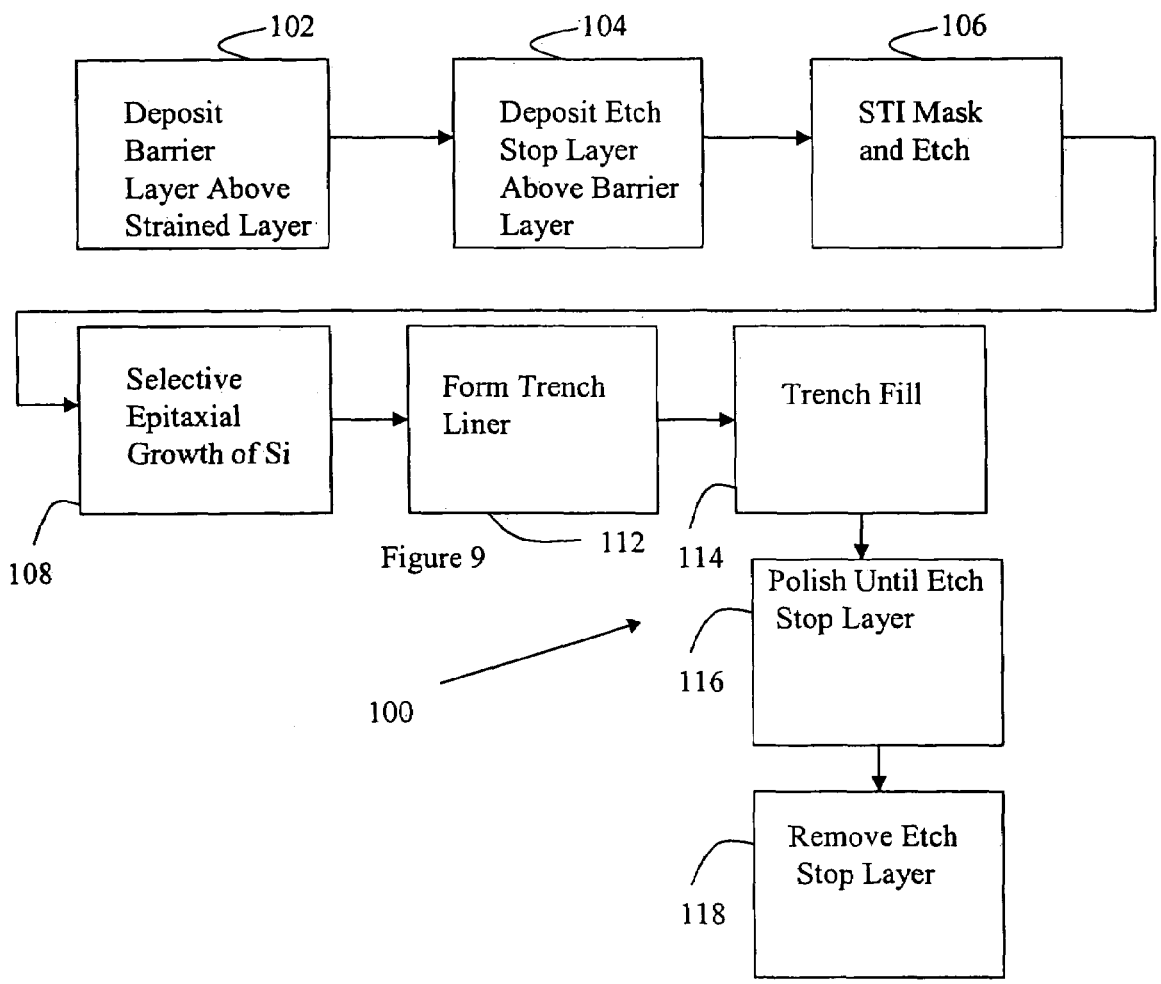
FIG. 9 is a general block diagram showing a shallow trench isolation process for the portion illustrated in FIG. 1.

In FIG. 3, a film or buffer barrier layer 50 is provided on a top surface of layer 16 in a step 102 of process 100 (FIG. 9). Layer 50 is preferably deposited by chemical vapor deposition on top of layer 16 to a thickness of between approximately 200 and 400 Å. Barrier layer 50 is preferably silicon dioxide and can alternatively be thermally grown above layer 16. Layer 16 serves as a buffer layer and can be thermally grown in a conventional high temperature process by heating to approximately 1000° C. in an oxygen atmosphere. Alternatively, any number of lower temperature deposition and growth processes can be utilized.

Figures 4, 5:
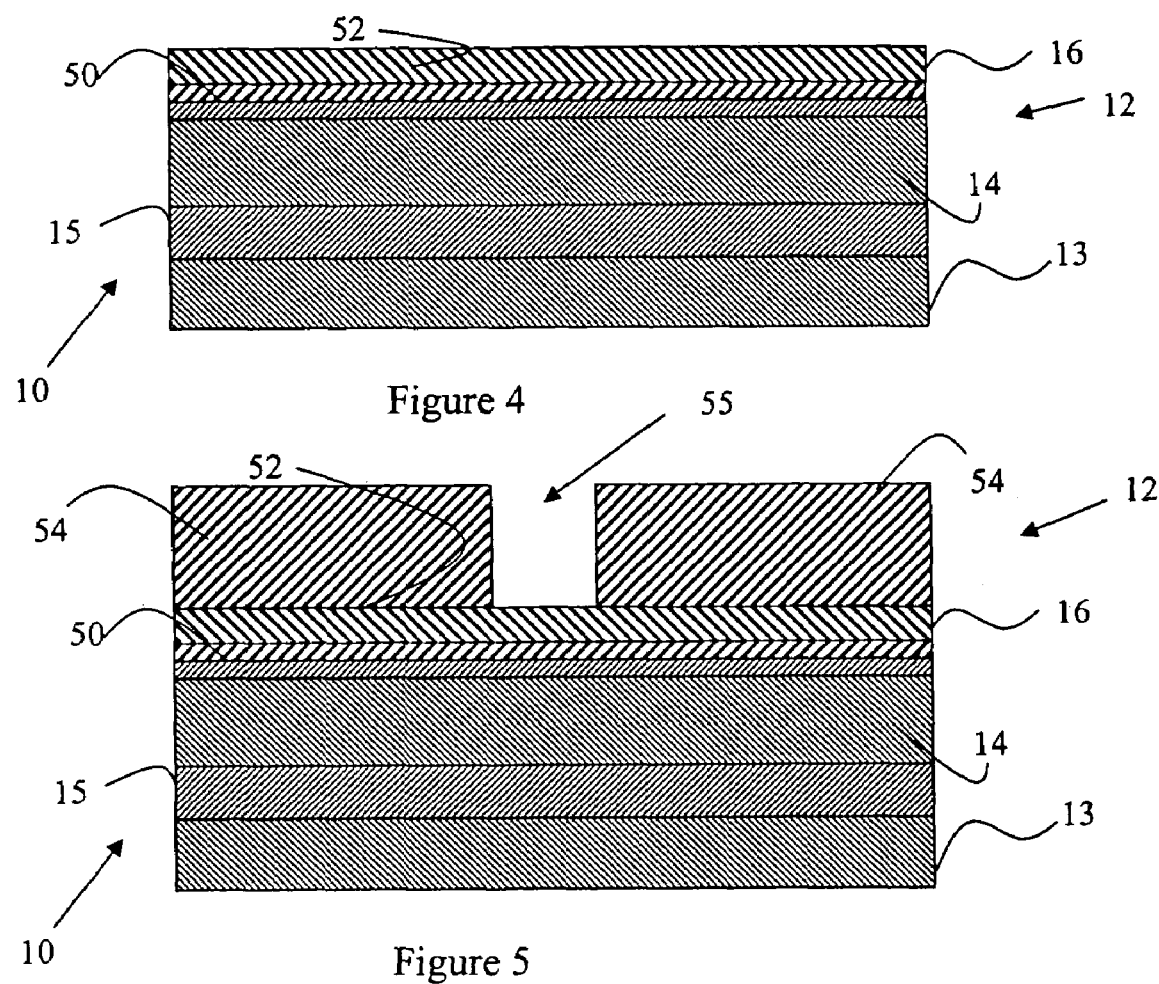
FIG. 4 is a cross-sectional schematic view of the portion illustrated in FIG. 3, showing a mask layer deposition step.
FIG. 5 is a cross-sectional schematic view of the portion illustrated in FIG. 4, showing a lithographic patterning step.

In FIG. 4, a barrier or hard mask layer 52 is provided over a top surface of barrier layer 50 in a step 104 of process 100 (FIG. 9). Preferably, mask layer 52 is silicon nitride ($Si_3N_4$) provided at a thickness of between approximately 1000 and 3000 Å by a deposition or thermal growth process. Preferably, mask layer 52 is provided by CVD. Alternatively, a silicon oxynitride (SiON) or other mask material can be utilized for layer 52.

A low pressure plasma enhanced chemical vapor deposition (PECVD) process can also be utilized. The PECVD process for depositing nitride uses silane ($SiH_4$), nitrogen ($N_2$), and ammonia ($NH_3$) with a power of between approximately 550 and 650 watts at 400° C. A conventional thermal nitride process using a dichlorosilane ($SiH_2Cl_2$), ammonia ($NH_3$) and nitrogen ($N_2$) mixture at a high temperature (e.g., 600° C. or above) can also be used. An ammonia ($NH_3$) silane ($SiH_4/N_2$) mixture plasma, as opposed to a $N_2/NH_3/SiCl_2H_2$ associated with conventional CVD or growth process, can also be used to form mask layer 52.

In FIG. 5, a photoresist layer 54 is spun on a top surface of mask layer 52 in a step 106 of process 100 (FIG. 9). Preferably, photoresist layer 54 is any commercially available i-line or deep UV photoresist such as (Shipley Corp., Massachusetts) SPR 955 (i-line) UV5 (deep UV). In FIG. 5, photoresist layer 54 is selectively removed via a photolithographic process to leave an aperture 55 in accordance with a step 106 (FIG. 9) of process 100.

Any conventional lithographic process can be used to form aperture 55. Aperture 55 can be between approximately 150 nm and 300 nm Å wide. Patterned layer 54 serves as an STI definition mask.

Figure 6:
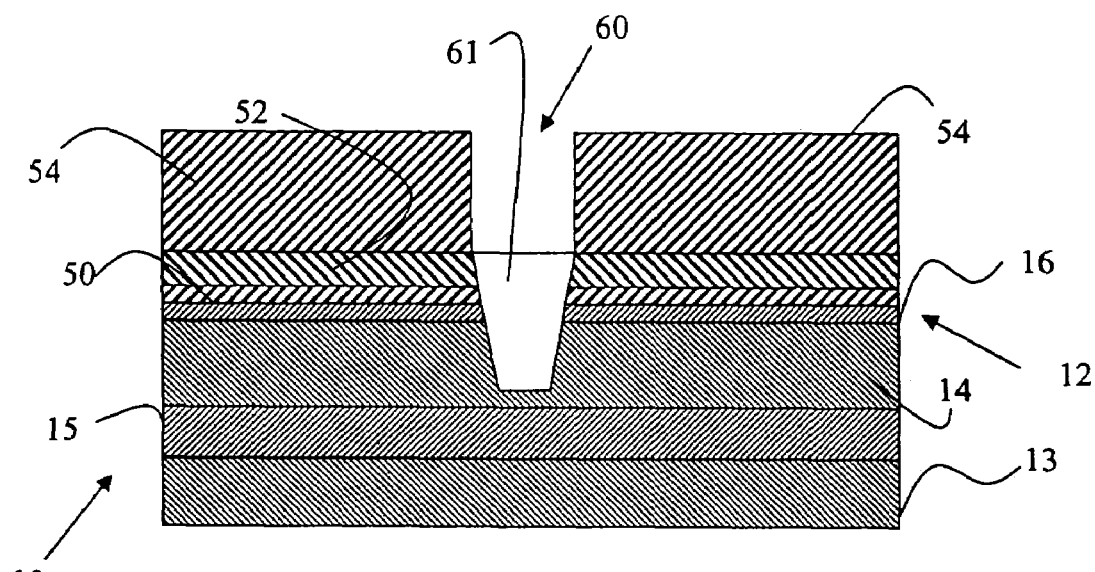
FIG. 6 is a cross-sectional schematic view of the portion illustrated in FIG. 2, showing a selective etching step for forming a trench.

In FIG. 6, mask layer 52 is etched via a dry-etching process so that an aperture 60 reaches barrier layer 50 in accordance with a step 106 of process 100 (FIG. 9). The dry-etching process is selective to silicon nitride with respect to the oxide of layer 50. Layer 54 can be stripped after layer 52 is etched.

In FIG. 6, the etch process is changed to etch through silicon dioxide material and layer 50 is etched so that aperture 60 reaches layer 16 in accordance with step 106 of process 100 (FIG. 9). Aperture 60 is dimensioned similar to aperture 55. Layer 50 can be etched in a dry etching process. Alternatively, other etching techniques can be utilized to remove selected portions of layer 50. Photoresist layer 54 can be removed before or after layer 50 is etched.

Figure 7:
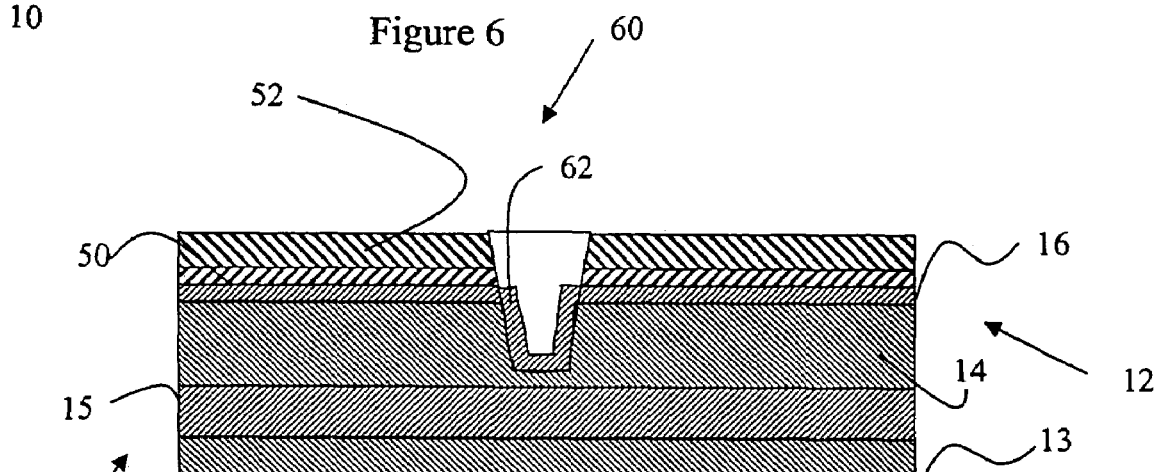
FIG. 7 is a cross-sectional schematic view of the portion illustrated in FIG. 6, showing a selective epitaxial growth step.

In FIG. 7, the etch process is changed to etch through silicon material. Strained silicon layer 16 can be removed in accordance with a dry-etching process so that aperture 60 reaches layer 14. Layer 14 is etched through to form a trench for shallow trench isolation structure 38 (FIG. 1) in accordance with step 106 of process 100 (FIG. 9). The trench preferably has a width corresponding to that of aperture 60. The trench preferably has a depth of between approximately 1500 and 3000 Å and a width of 300 nm or less.

The trench can have a trapezoidal cross-sectional shape with the narrower portion being at the bottom. Alternatively, the trench can have a more rectangular or other cross-sectional shape. Layer 14 is preferably etched in a dry-etching process to form the trench. Layer 14 can be etched in the same step used to etch layer 16.

Although described as being etched in a dry etching process, the trench can be formed in any process suitable for providing an aperture in layers 14 and 16. In one embodiment, the aperture for the trench is provided all the way through layer 14 to substrate 13. Alternatively, the bottom of the trench associated with the aperture may not reach substrate 13, depending upon the thickness of layer 14. In an embodiment in which substrate 13 is not provided, layer 14 is deeper than the trench associated with the aperture. The trench is preferably deeper than N well 31.

In FIG. 7, a conformal layer 62 is formed in the trench associated with aperture 60 in a step 108 of process 100 by selective epitaxial growth. In one embodiment, layer 62 is a semiconductor or metal layer that can be formed at a low temperature (e.g., below approximately 600° C.). Layer 62 is preferably a layer that can be oxidized to form an insulative material such as an oxide liner. Most preferably, layer 62 is a 50–200 Å thick silicon layer deposited by CVD at a temperature of 500–600° C. Layer 62 is deposited in accordance with step 108 of process 100 (FIG. 9).

In another embodiment, layer 62 is a metal or semiconductor material deposited by atomic layer deposition (ALD) at low temperature. For example, layer 62 can be a silicon layer that can be non-amorphous and preferably single crystalline.

Layer 62 is preferably provided on sidewalls of the trench associated with aperture 60 of layers 14, 16, 50 and 52. Layer 62 is not provided on a top surface of layer 54. Layer 62 can be provided after layer 54 and/or layer 52 are removed.

Figure 8:
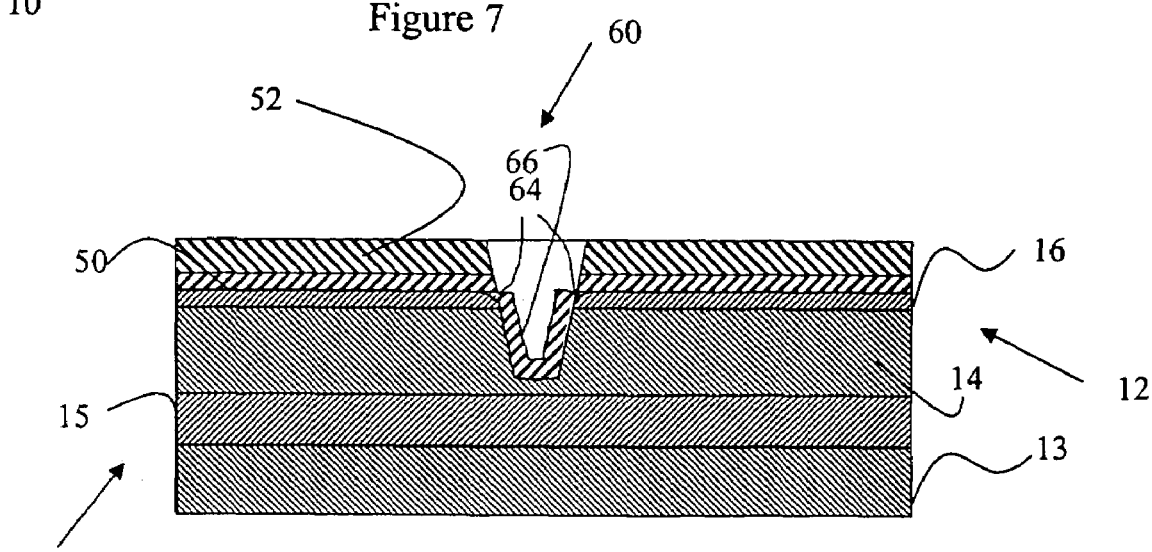
FIG. 8 is a cross-sectional schematic view of the portion illustrated in FIG. 6, showing a liner formation step.

In FIG. 8, layer 62 is converted to an insulative material such as a liner oxide material 66. Preferably, layer 62 is formed into liner oxide material 66 in an oxidation process at a temperature of approximately 900° C. or less in a step 112 of process 100. Preferably, the oxidation process creates rounded corners 64. Germanium outdiffusion is reduced due to the barrier associated with layer 62. Preferably, the entire layer 62 is converted into liner oxide material 66.

Preferably, liner oxide material is a silicon oxide or silicon dioxide material formed by oxidizing a semiconductor or metal layer. In one embodiment, liner oxide material 66 is approximately 100–200 Å thick. In one embodiment, layer 54 is stripped before the formation of liner oxide material 66. In a preferred embodiment, layers 50 and 52 are not stripped until after the trench is filled.

In FIG. 1, insulative material can be blanket deposited over layer 52 and within the trench associated with aperture 60 (FIG. 7) to form structure 38 (e.g., in a trench fill process). The insulative material is preferably silicon dioxide deposited by CVD such as in a high density plasma (HDP) process. Preferably, the insulative material is deposited in a tetraethylorthosilicate (TEOS) process. Alternatively, a boron phosphate silicon glass (BPSG) process can be utilized. The insulative material is preferably between approximately 2000 and 8000 Å thick.

The insulative material is removed by polishing/etching until a top surface of layer 52 (FIG. 7) is reached. The removal of the insulative material leaves oxide material within the trench associated with aperture 60 in a step 114 of process 100. The insulative material can be removed by a number of stripping or etching processes. The insulative material can be alternatively removed from above layer 52 by dry-etching.

In FIG. 1, after insulative material is provided in the trench associated with aperture 60, layers 52 and 50 can be removed and gate structures 32A–B can be provided. Layer 50 can be removed by wet etching with hydrofluoric acid (HF) solutions. Gate structures 32A–B can be conventional MOSFET gate structures, such as metal over oxide gate structures or polysilicon over oxide gate structures.

Various changes can be made to process 100 and to the material for layers 50 and 52 without departing from the scope of the invention. For example, in one embodiment, an amorphous silicon capping layer can be provided between layers 50 and 52. In this embodiment, the amorphous silicon layer between layers 50 and 52 is 100–400 Å thick and layer 50 is 100–400 Å thick. The amorphous silicon capping layer can be deposited by CVD or PVD.

Layer 50 separates the strained silicon layer 16 from the amorphous silicon capping layer and preserves the strained silicon capping layer from being relaxed. In another embodiment, the amorphous silicon layer can be a polysilicon layer.

The amorphous silicon capping layer serves as a sacrificial layer which is consumed during cleaning, implanting and oxidation steps. The amorphous silicon capping layer prevents consumption of layer 16 during cleaning, implanting and oxidation steps, thereby resulting in more acceptable thickness variations for layer 16. The etching steps associated with aperture 55 are adjusted to etch through the amorphous silicon capping layer. The residual sacrificial amorphous silicon layer can be removed before field and channel implants and the remainder of layer 50 can be used as a sacrificial oxide layer for field and channel implants.

In another embodiment, an amorphous silicon capping layer can be provided above layer 52 similar to the amorphous silicon capping layer discussed above. As discussed above, the amorphous silicon capping layer can be 100–400 Å thick and layer 50 is 100–400 Å thick in this embodiment. The amorphous silicon layer prevents consumption of layer 16 during cleaning and oxidation steps.

In yet another embodiment, a silicon germanium capping layer can be provided above layer 16 and below layer 50. Similar to the amorphous silicon layer described above, the silicon germanium capping layer protects layer 16 from consumption during oxidation, implanting and cleaning steps. In addition, the capping layer reduces process variations associated with layer 16.

The silicon germanium capping layer can be removed before field and channel implants. A sacrificial oxide layer can be formed thermally on the silicon layer 16 for field and channel implants. The sacrificial oxide layer can be removed by a wet etch with HF solutions before gate oxide formation. The silicon germanium layer is preferably a relaxed layer approximately 100 Å to 400 Å thick with the same germanium content as layer 14. The silicon germanium capping layer can be grown epitaxially on layer 16 by CVD or MBE. The use of a silicon germanium cap layer also advantageously increases the available critical thickness associated with layer 16 from about 170 Å to approximately 340 Å.

It is understood that while the detailed drawings, specific examples, and particular values given provide a preferred exemplary embodiment of the present invention, it is for the purpose of illustration only. The shapes and sizes of trenches are not disclosed in a limiting fashion. The method and apparatus of the invention is not limited to the precise details and conditions disclosed. Various changes may be made to the details disclosed without departing from the spirit of the invention, which is defined by the following claims.

What is claimed is:

1. A method of manufacturing an integrated circuit having trench isolation regions in a substrate including germanium, the method comprising:
   providing a substrate comprising a silicon-germanium layer and a strained silicon layer provided above the silicon-germanium layer;
   forming a mask layer above the substrate;
   selectively etching the mask layer to form apertures associated with locations of the trench isolation regions;
   forming trenches in the substrate at the locations, the trenches having sidewalls;
   providing a semiconductor or metal layer directly in contact with the sidewalls such that the semiconductor or metal layer is in direct contact with the silicon-germanium layer and the strained silicon layer; and
   converting the semiconductor or metal layer in the trenches of the substrate into oxide liners.

2. The method of claim 1, further comprising providing an insulative material in the trenches to form the trench isolation regions.

3. The method of claim 2, further comprising removing the insulative material until the mask layer is reached.

4. The method of claim 1, further comprising:
   providing a low temperature process oxide layer above the substrate and an amorphous capping layer above the oxide layer.

5. The method of claim 1, wherein the amorphous capping layer is amorphous silicon.

6. The method of claim 1, wherein the semiconductor or metal layer includes silicon material.

7. The method of claim 1, further comprising:
   providing a silicon nitride layer above the substrate and providing an amorphous capping layer above the silicon nitride layer.

8. The method of claim 1, wherein the forming oxide liners step is an oxidation process.

9. A method of forming shallow trench isolation regions in a strained semiconductor layer, the method comprising:
   providing a hard mask layer above the strained semiconductor layer;
   providing a photoresist layer above the hard mask layer;
   selectively removing portions of the photoresist layer at locations in a photolithographic process;
   removing the hard mask layer at the locations;
   forming trenches in the strained semiconductor layer under the locations;
   providing a conformal semiconductor layer in the trenches in direct contact with the strained semiconductor layer; and
   oxidizing the conformal semiconductor layer to form a liner in the trenches.

10. The method of claim 9, further comprising:
    providing a pad oxide layer above a strained silicon layer before the providing a hard mask layer step.

11. The method of claim 10 further comprising:
    removing the pad oxide layer at the locations before the forming trenches step.

12. The method of claim 9, further comprising:
    providing an insulative material in the trenches to form the shallow trench isolation regions; and
    removing the hard mask layer.

13. The method of claim 9, further comprising:
    providing a germanium-containing layer above the strained semiconductor layer.

14. The method of claim 13, wherein the strained semiconductor layer is at least 200 Å thick.

15. The method of claim 14, wherein the germanium-containing cap layer is 100–400 Å.

16. The method of claim 15, wherein the oxide liner is silicon dioxide grown in an oxygen atmosphere.

17. A method of forming a liner in a trench comprising:
    providing a strained layer above a germanium containing layer;
    selectively etching the germanium containing layer and the strained layer to form the trench;
    providing a semiconductor layer in the trench such that the semiconductor layer is in direct contact with the germanium containing layer and the strained layer; and
    converting the semiconductor layer into an oxide liner such that substantially all of the semiconductor layer is consumed during the conversion.

18. The method of claim 17, wherein the step of providing a semiconductor layer in the trench is performed at a temperature below 600° C.

19. The method of claim 17, wherein the oxide liner is 100–200 Å thick.

* * * * *